US009487746B2

United States Patent
Aragaki (10) Patent No.: US 9,487,746 B2
(45) Date of Patent: Nov. 8, 2016

(54) CELL DIVISION TRACKING APPARATUS AND METHOD OF THE SAME, AND NON-TRANSITORY COMPUTER READABLE STORAGE MEDIUM TO STORE A CELL DIVISION TRACKING PROGRAM

(71) Applicant: OLYMPUS CORPORATION, Shibuya-ku, Tokyo (JP)

(72) Inventor: Hideya Aragaki, Akishima (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 14/588,188

(22) Filed: Dec. 31, 2014

(65) Prior Publication Data

US 2015/0111291 A1   Apr. 23, 2015

Related U.S. Application Data

(63) Continuation of application No. PCT/JP2013/068285, filed on Jul. 3, 2013.

(30) Foreign Application Priority Data

Jul. 5, 2012   (JP) ................................. 2012-151722

(51) Int. Cl.
*G06K 9/00*   (2006.01)
*C12M 1/34*   (2006.01)
(Continued)

(52) U.S. Cl.
CPC ............. *C12M 41/46* (2013.01); *C12M 41/48* (2013.01); *G06K 9/0014* (2013.01);
(Continued)

(58) Field of Classification Search
CPC .................................. G06K 9/00; G06T 7/00
USPC ......... 382/130, 107, 173, 236; 348/169–172, 348/352; 435/376, 288.7
See application file for complete search history.

(56) References Cited

U.S. PATENT DOCUMENTS 8,129,990 B2 *   3/2012   Yamamoto ......... G01N 21/6458
                                                                 324/300
2003/0108230 A1   6/2003   Miyano et al.

FOREIGN PATENT DOCUMENTS

JP   2000101995 A   4/2000
JP   2001258599 A   9/2001
(Continued)

OTHER PUBLICATIONS

International Search Report (ISR) dated Sep. 10, 2013 issued in International Application No. PCT/JP2013/068285.
(Continued)

*Primary Examiner* — Abolfazl Tabatabai
(74) *Attorney, Agent, or Firm* — Holtz, Holtz & Volek PC (57) ABSTRACT

A cell division tracking apparatus includes a control unit, a search range setting unit, a daughter cell judgment unit. The control unit tracks division processes of the cells based on a cell image group composed of the cell images. The search range setting unit sets a search range to search for daughter cell regions corresponding to daughter cells resulting from a division of a mother cell based on the mother cell region detected by the mother cell detection unit. The daughter cell judgment unit judges whether the cell regions are the daughter cell regions based on a region in which regions of the cell overlap the search range regarding the cell images collected at and after a detection of the mother cell region.

9 Claims, 9 Drawing Sheets (51) Int. Cl.
  *G06T 7/20* (2006.01)
  *G06T 7/00* (2006.01)
  *C12M 1/36* (2006.01)
  *C12N 5/00* (2006.01)

(52) U.S. Cl.
  CPC .............. *G06T 7/0012* (2013.01); *G06T 7/20* (2013.01); *G06T 2207/10016* (2013.01); *G06T 2207/10056* (2013.01); *G06T 2207/20144* (2013.01); *G06T 2207/20152* (2013.01); *G06T 2207/30024* (2013.01)

(56) References Cited

FOREIGN PATENT DOCUMENTS

| JP | 2006238802 A | 9/2006 |
|---|---|---|
| JP | 2007327843 A | 12/2007 |

OTHER PUBLICATIONS

International Preliminary Report on Patentability (IPRP) including Written Opinion dated Jan. 15, 2015, issued in parent International Application No. PCT/JP2013/068285.

Extended European Search Report dated Apr. 26, 2016, issued in counterpart European Application No. 13813166.9.

Debeir, et al., "Videomicroscopic Extraction of Specific Information on Cell Proliferation and Migration in Vitro", Experimental Cell Research, Academic Press, US, vol. 314, No. 16, Oct. 1, 2008; pp. 2985-2998.

Huh, et al., "Automated Mitosis Detection of Stem Cell Populations in Phase-Contrast Microscopy Images", IEEE Transactions on Medical Imaging, vol. 30, No. 3, Mar. 1, 2011; pp. 586-596.

Huh, et al., "Mitosis Detection of Hematopoietic Stem Cell Populations in Time-Lapse Phase-Contrast Microscopy Images", International Symposium on Biomedical Imaging (ISBI), 9th IEEE, May 2, 2012; pp. 390-393.

\* cited by examiner

CELL DIVISION TRACKING APPARATUS AND METHOD OF THE SAME, AND NON-TRANSITORY COMPUTER READABLE STORAGE MEDIUM TO STORE A CELL DIVISION TRACKING PROGRAM

CROSS-REFERENCE TO RELATED APPLICATIONS

This application is a Continuation application of PCT Application No. PCT/JP2013/068285, filed Jul. 3, 2013 and based upon and claiming the benefit of priority from prior Japanese Patent Application No. 2012-151722, Jul. 5, 2012, the entire contents of all of which are incorporated herein by reference.

BACKGROUND OF THE INVENTION

1. Field of the Invention

The present invention relates to a cell division tracking apparatus and a method of the same to track the process of cell division on the basis of, for example, a cell image group collected by the use of a microscope, and a non-transitory computer readable storage medium to store a cell division tracking program.

2. Description of the Related Art

Heretofore, in what is known as life-science fields, various cell analysis based on images of cells (hereinafter referred to as cell images) photographed by the use of a microscope have been conducted.

For example, in the studies of stem cells such as ES cells and iPS cells, cell analysis intended for the elucidation of cell differentiation mechanisms and the discovery and development of drugs have been conducted. That is, the following analysis (hereinafter referred to as cell analysis) is conducted in these studies: cell differentiation processes and morphological feature changes are observed on the basis of cell images (hereinafter referred to as a cell image group) collected by time-lapse photography in a time-series manner, and differences in characteristics of cells are investigated.

In the above cell analysis, automation of troublesome operations such as the screening of individual cells that has heretofore been visually performed is becoming possible by the application of image processing technology such as image recognition. If this image processing technology is applied, it is possible for individual cells in the cell image to be discerned, and, for example, to discern morphological features of cells, the number of cells and their changes, and the movement amount and activity degree of the cells by tracking individual cells.

For the analysis of the process of cell division, it is necessary to correctly detect the phenomenon of cell division in the cell image, and correctly recognize the relationship between a cell before division and two daughter cells that emerge as a result of the division. Visually performing the operation of correctly recognizing the relationship requires a significantly complex operation. Therefore, automation of cell analysis that applies an image recognition technique and an image tracking technique has been requested.

Under these circumstances, Jpn. Pat. Appln. KOKAI Publication No. 2007-327843, for example, has been suggested as a technique for tracking cell division. According to the technique disclosed in Jpn. Pat. Appln. KOKAI Publication No. 2007-327843, individual cell regions are specified by cell detection processing from a series of collected cell image groups, a cell feature value is measured for each of the specified cell regions, and the cell regions showing the same cells between frames of the cell image groups are specified among the cell regions on the basis of the cell feature value. During this processing, tracking processing of cell division, that is, processing of associating mother cells before division with two daughter cells after division is performed.

In this tracking processing, neighboring cell regions that are likely to be daughter cells are extracted on the basis of information (e.g., information regarding the distance between the centroids of the regions; hereinafter referred to as relative position information) indicating the positional relation between a cell region targeted for tracking (hereinafter referred to as a tracking target cell region) and cell regions therearound (hereinafter referred to as neighboring cell regions). The cell feature value of each cell region and its change rate are judged on the basis of a preset judgment condition, and the neighboring cell regions that fulfill the judgment condition are specified as daughter cells.

BRIEF SUMMARY OF THE INVENTION

A cell division tracking apparatus according to aspect of the present invention comprises an imaging unit which images cells, a control unit which images the cells by the imaging unit multiple times to acquire a cell images, and tracks division processes of the cells on the basis of a cell image group composed of the cell images, a cell detection unit which detects a cell region which is a region showing the cells in each of the cell images, a mother cell detection unit which detects a mother cell region corresponding to a mother cell immediately before cell division in each of the cell images, a search range setting unit which sets a search range to search for daughter cell regions corresponding to daughter cells resulting from the division of the mother cell on the basis of the mother cell region detected by the mother cell detection unit, and a daughter cell judgment unit which judges whether the cell regions are the daughter cell regions on the basis of a region in which the cell regions overlap the search range regarding the cell images collected at and after the detection of the mother cell region.

A cell division tracking method according to aspect of the present invention comprises by computer processing, by computer processing, acquiring a multiple cell images by an imaging unit multiple times to image a cell, tracking division processes of the cells on the basis of a cell image group composed of the cell images, detecting a cell region which is a region showing the cells in each of the cell images, detecting a mother cell region corresponding to a mother cell immediately before cell division in each of the cell images, setting a search range to search for daughter cell regions corresponding to daughter cells resulting from the division of the mother cell on the basis of the detected mother cell region, and judging whether the cell regions are the daughter cell regions on the basis of a region in which the cell regions overlap the search range regarding the cell images collected at and after the detection of the mother cell region.

A non-transitory computer readable storage medium to store a cell division tracking program comprises an imaging function which images cells, a control function which images the cells by the imaging function multiple times to acquire a cell images, and tracks division processes of the cells on the basis of a cell image group composed of the cell images, a cell detection function which detects a cell region which is a region showing the cells in each of the cell images, a mother cell detection function which detects a mother cell region corresponding to a mother cell immediately before cell division in each of the cell images, a search range setting function which sets a search range to search for daughter cell regions corresponding to daughter cells resulting from the division of the mother cell on the basis of the mother cell region detected by the mother cell detection function, and a daughter cell judgment function which judges whether the cell regions are the daughter cell regions on the basis of a region in which the cell regions overlap the search range regarding the cell images collected at and after the detection of the mother cell region.

Additional advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

Figure 1:
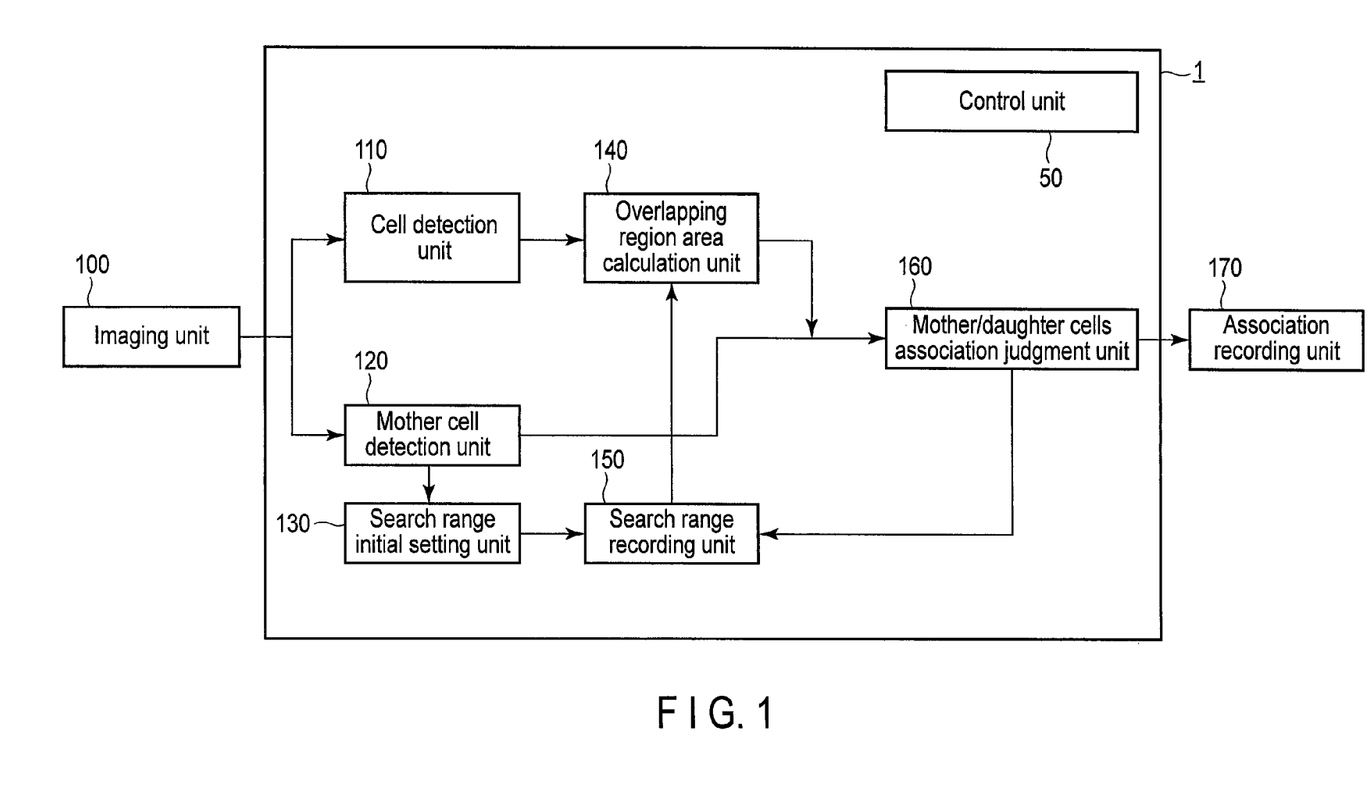
FIG. 1 is a diagram showing a configuration example of a cell division tracking apparatus according to a first embodiment of the present invention.
Figure 2:
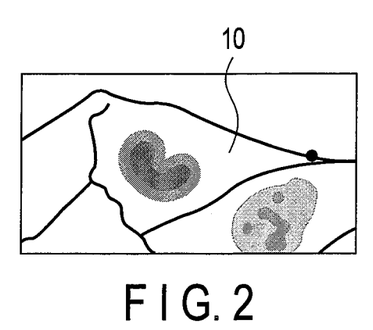
FIG. 2 is a diagram showing a cell image in the process of cell division collected by photography using a bright field microscope.

Hereinafter, a cell division tracking apparatus and a cell division tracking program according to a first embodiment of the present invention will be described with reference to the drawings. FIG. 1 shows a configuration example of a cell division tracking apparatus according to the first embodiment of the present invention. FIG. 2 to FIG. 7 show cell images in the process of cell division collected by photography using a bright field microscope.

A cell division tracking apparatus (hereinafter referred to as the present apparatus) 1 includes a cell detection unit 110, a mother cell detection unit 120, a search range initial setting unit (search range setting unit) 130, an overlapping region area calculation unit 140, a search range recording unit 150, a mother/daughter cells association judgment unit (daughter cell judgment unit) 160, and a control unit 50. An imaging unit 100 and an association recording unit 170 are connected to the present apparatus 1.

The control unit 50 is a system controller which is connected to each of the units of the present apparatus 1 and which takes overall control of these units.

The imaging unit 100 includes an image pickup device such as a CCD and an A/D converter, and is, for example, a camera attached to a phase contrast microscope. This camera converts a phase difference image of cells acquired by photography using, for example, the phase contrast microscope to a digital signal, and outputs this signal as, for example, an 8-bit (256-tone) monochrome original image signal.

The imaging unit 100 images an observation target cell group multiple times by time-lapse photography. As a result of this imaging, the imaging unit 100 outputs a cell image group composed of cell images collected in a time-series manner to the present apparatus 1. The cell image group is composed of cell images collected by imaging the observation target cell group multiple times in a predetermined photography period.

The phase contrast microscope is a microscope that uses diffraction phenomena of light. The phase contrast microscope obtains, as contrast, a phase difference (optical path difference) of light passing through substances having different refractive indexes. The phase contrast microscope is therefore suitable for the observation of subjects such as transparent cells or microorganisms.

An image acquired by photography using the phase contrast microscope is characterized by the generation of strong contrast called a halo (artifact) on the boundary between a background region and a sample. The halo mostly appears as aura-like light at the boundary between a background region and each cell region in a cell image acquired by photography using the phase contrast microscope.

For the photography by the imaging unit 100, other bright field microscopes such as a differential interference contrast microscope (DIC) may be used instead of the phase contrast microscope.

In the present first embodiment, the imaging unit 100 photographs the cell group about every 30 minutes before the start of cell division. Image numbers are given to the cell images collected by the photography in the order of photography so that the images are distinguishable.

For example, a signal of an image obtained Ni×30 minutes after the start of photography indicates a cell image of an image number Ni. The cell image at the start of photography is a cell image of an image number 0.

The cell detection unit 110 divides the region by performing later-described "region dividing processing" for each of the cell images input to the present apparatus 1, and judges whether each divided region resulting from the region division is a cell region or a background region (non-cell region). That is, the cell detection unit 110 performs "cell detection processing" to specify the cell region where each cell in the cell image is located. Divided region images which are divided into regions by the cell detection unit 110 and which are cell images having the divided regions that are specified as cell regions and background regions are output to the overlapping region area calculation unit 140.

The "region dividing processing" is processing to divide a pixel collection constituting an observation target cell image into one or more pixel collections (regions) which are similar in feature to each other and which are spatially close to each other.

In general, the cell image obtained through the phase contrast microscope has a high luminance on the cell boundary and has a low luminance inside the cell. In view of this characteristic, in the present first embodiment, the region dividing processing that uses a watershed method (watershed region dividing method) which is a known region dividing method is performed to cut (divide) a cell image into cell regions. The watershed method performs division based on a luminance value gradient of an image, and performs division that uses, as a dividing line, a part in the image which is high in luminance value and which has a steep luminance value gradient, that is, the boundary of the cells.

The cell detection unit 110 gives a region ID=Ns (Ns is an integer equal to or more than 0) to each of the divided regions resulting from the region dividing processing as a region number by known labeling processing, and uses the region ID as a pixel value to generate cell images divided into regions. A region ID=0 is given to the background region.

The known technique to be used as a region dividing technique is not necessarily limited to the watershed method. Any technique that can divide a cell region into regions with proper accuracy may be used.

The "cell detection processing" specifies whether each divided region resulting from the above-mentioned region dividing processing is a cell region or a background region (non-cell region). However, in contrast with the cell region, the background region has a significantly small variation of luminance value in the region. Therefore, it is possible to calculate, for example, the average edge strength value for each divided region, and a region with an extremely low value can be specified as the background region.

The mother cell detection unit 120 specifies a mother cell region immediately before cell division which is present in the cell image, and outputs the image number of this cell image, a later-described mother cell ID number, and positional information and size information regarding the mother cell region. The processing by the mother cell detection unit 120 is referred to as mother cell detection processing.

Figure 3:
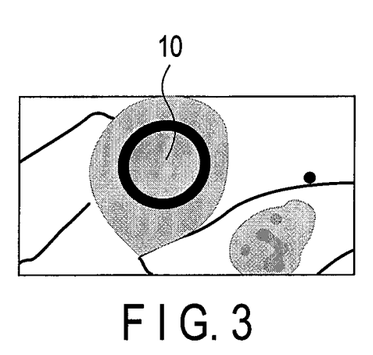
FIG. 3 is a diagram showing a cell image in the process of cell division collected by photography using the bright field microscope.

In general, the shape of a cell is rapidly rounded and thickened at a stage immediately before a time M (a time at which cell division occurs) in a cell period. More specifically, a mother cell 10 shifts from the state shown in FIG. 2 to the state shown in FIG. 3. At the same time, in the cell image acquired by photography using the phase contrast microscope, a halo (artifact) strongly appears in the vicinity of the boundary of the cell region as shown in FIG. 3.

Figure 4:
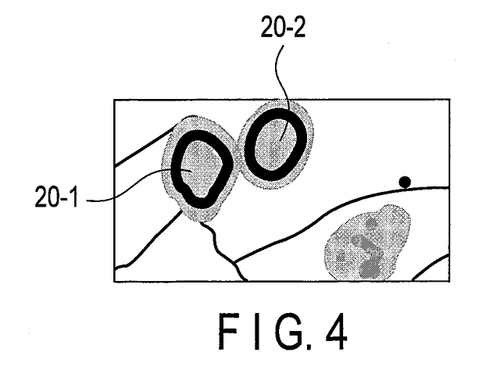
FIG. 4 is a diagram showing a cell image in the process of cell division collected by photography using the bright field microscope.
Figure 5:
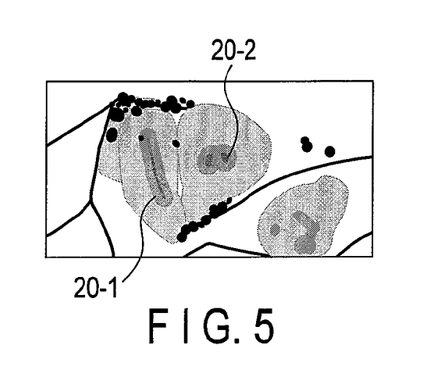
FIG. 5 is a diagram showing a cell image in the process of cell division collected by photography using the bright field microscope.
Figure 6:
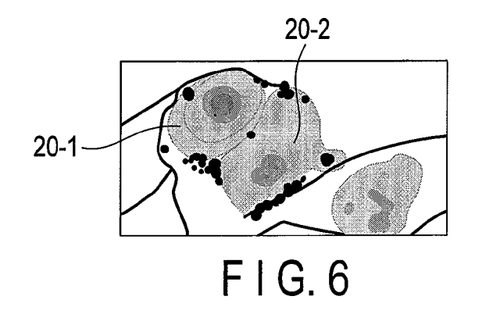
FIG. 6 is a diagram showing a cell image in the process of cell division collected by photography using the bright field microscope.
Figure 7:
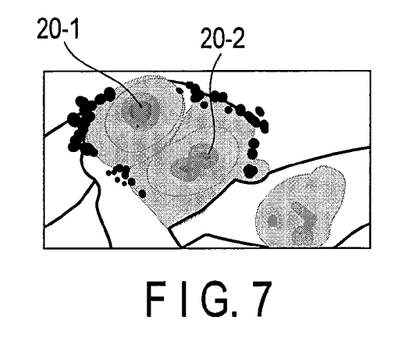
FIG. 7 is a diagram showing a cell image in the process of cell division collected by photography using the bright field microscope.

The mother cell 10 then divides into two daughter cells 20-1 and 20-2 as shown in FIG. 4. At a stage immediately after the cell division, the daughter cells 20-1 and 20-2 are substantially circular as shown in FIG. 4. The daughter cells 20-1 and 20-2 are then deformed from the substantially circular shape as shown in FIG. 5 to FIG. 7.

In the present first embodiment, in view of the property of the mother cell that has a substantially circular shape at a stage immediately before cell division, a "circular kernel" modeled on the circular shape of the cell immediately before cell division is set. In the present first embodiment, all the pixels in the cell image are filtered by the use of the circular kernel, and the value of the output of this filtering processing is evaluated to detect a mother cell region having a substantially circular shape.

Figure 8:
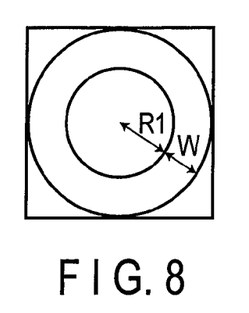
FIG. 8 is a diagram showing an example of a circular kernel used in filtering processing for detecting a mother cell region.

FIG. 8 shows an example of a circular kernel used in filtering processing for detecting the mother cell region. "R1" shown in FIG. 8 indicates the inside radius of the circular kernel, and "R1+W" indicates the outside radius of the circular kernel.

The inside radius R1 is set to a dimension slightly smaller than the size of an average mother cell region present in the cell image. An inside/outside radius difference W is set to be slightly larger than the width of a mother cell boundary (halo). Both the inside radius R1 and the inside/outside radius difference W are preset parameters. The lengthwise and crosswise dimensions of the circular kernel are, for example, "2×(R1+W) pixels".

In the circular kernel according to the present first embodiment, a "filter coefficient=1" is set for the pixels in the region which is "equal to or more than the inside radius R1 and equal to or less than the outside radius (R1+W)", and a "filter coefficient=0" is set for the other pixels.

The mother cell detection unit 120 performs filtering processing based on the above-mentioned circular kernel for the cell image. The output value of this filtering processing is a "luminance average value" obtained if a "luminance cumulative value" in which the values of the pixels in the region of the "filter coefficient=1" in the circular kernel are added up is divided by the filter coefficient sum.

The mother cell detection unit 120 performs the above-mentioned filtering processing for all the pixels constituting the cell image, and calculates a luminance average value for each pixel. The mother cell detection unit 120 detects the pixel which is higher than a preset threshold and in which the luminance average value shows a value higher than that of neighboring pixels (shows a peak value). The position of this detected pixel is specified as the central coordinates of the substantially circular mother cell region.

Figure 9:
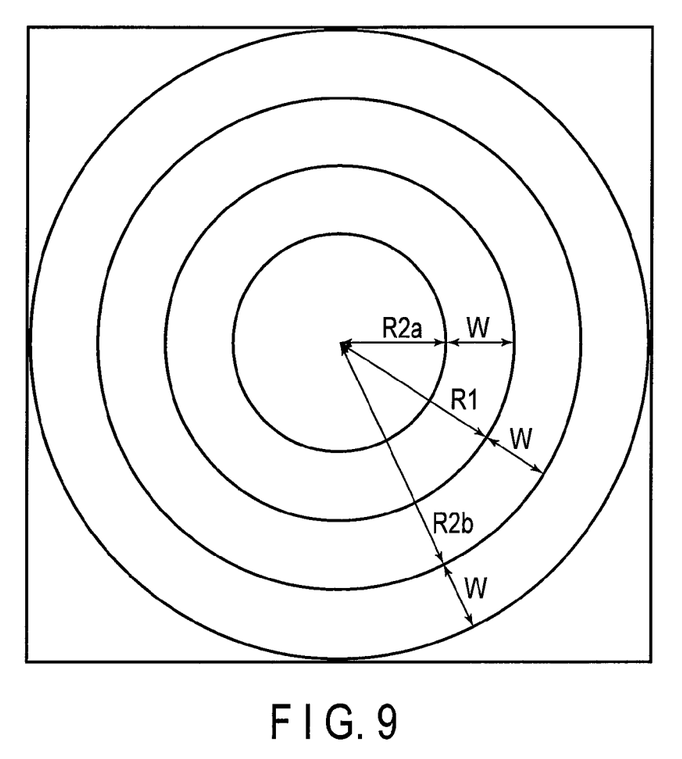
FIG. 9 is a diagram showing an example of a circular kernel used in filtering processing for specifying the dimensions of a mother cell region.

The mother cell detection unit 120, specifies the dimensions of the mother cell region. FIG. 9 shows an example of a circular kernel used in filtering processing for specifying the dimensions of the mother cell region. As shown in FIG. 9, in the present first embodiment, a first radius R2a, a second radius R1, and a third radius R2b are set so that R2a<R1<R2b, and three kinds of circular kernels are set accordingly: a first circular kernel having the first radius R2a, a second circular kernel having the second radius R1, and a third circular kernel having the third radius R2b.

Although the dimensions of the circular kernels are set so that R2a+W=R1 and R1+w=R2b in the example shown in FIG. 9, the dimensions of the circular kernels are not exclusively set as above and may be set to any dimensions.

In the present first embodiment, the mother cell detection unit 120 performs the filtering processing by applying the three kinds of circular kernels to the mother cell region on the basis of the pixel on the central coordinates of the mother cell region detected by the above-mentioned processing. The mother cell detection unit 120 compares the output values of the filtering processing using the three kinds of circular kernels, specifies the radius of the circular kernel corresponding to the maximum value as the dimension of the mother cell, and generates size information indicating the dimensions of the mother cell region.

The mother cell detection unit 120 gives Nm (Nm is an integer equal to or more than 0) as the mother cell ID number to the mother cell region which has been detected by the above-mentioned series of processes and whose dimensions have been specified so that each mother cell region is distinguishable.

The search range initial setting unit 130 sets, as a "search range", the region where two daughter cells resulting from the division of the mother cell seem to be located (region where the daughter cells should be searched for), on the basis of the positional information and size information regarding the mother cell region output from the mother cell detection unit 120.

More specifically, the search range initial setting unit 130 sets, as the search range, the concentric region having a radius w1×R (w1 is a predetermined constant larger than 1.0) around the central coordinates of the mother cell region, on the basis of the size information (radius) regarding the mother cell region output from the mother cell detection unit 120.

The shape of the search range is not exclusively circular and may be set to any shape.

The search range recording unit 150 records the search range set by the search range initial setting unit 130 together with the mother cell ID number of the corresponding to the mother cell region and the image number of the cell image in which the mother cell has been detected.

The overlapping region area calculation unit 140 judges whether there are two or more cell regions overlapping the search range (hereinafter briefly referred to as overlapping regions) among the divided regions on a region-divided image regarding the cell images collected at the time and after the time (hereinafter referred to as at and after the time) of photographing the mother cell region to which the mother cell ID number has been given, on the basis of the search range, the mother cell ID number, and the image number recorded in the search range recording unit 150. If there are two or more overlapping regions, the overlapping region area calculation unit 140 calculates the area (number of pixels) of each overlapping region. The region ID of the overlapping region, the area of the overlapping region, the image number of the cell image in which the overlapping region is photographed, the mother cell ID number of the corresponding mother cell region, and the image number of the cell image in which the mother cell region is photographed are output to the mother/daughter cells association judgment unit 160.

If there is no overlapping region or there is only one overlapping region, it is considered that two daughter cells have not emerged because cell division is not completed at the photography time of this cell image or that division is insufficient because of poor accuracy of cell division.

Therefore, if there is no overlapping region or there is only one overlapping region, the overlapping region area calculation unit 140 performs no processing for the cell image of the corresponding frame, and performs processing for the cell image (of the next frame) collected in the following photography.

The mother/daughter cells association judgment unit 160 judges whether the cell image collected at and after the time the detection of the mother cell region is a daughter cell region on the basis of the region in which the cell region and the search range overlap each other. The mother/daughter cells association judgment unit 160 judges that the cell region is a daughter cell region if the area of the overlapping region of the cell region and the search range is equal to or more than a predetermined threshold. The mother/daughter cells association judgment unit 160 judges that the cell region is a daughter cell region on the basis of at least one of the size of the area of the overlapping region of the cell region and the search range, the roundness of the overlapping region, and the centroid of the overlapping region.

More specifically, the mother/daughter cells association judgment unit 160 judges whether each overlapping region is a daughter cell resulting from cell division on the basis of the overlapping area. That is, the mother/daughter cells association judgment unit 160 specifies top two overlapping regions largest in area among the multiple overlapping regions. If the area of each of these overlapping regions is equal to or more than a "predetermined threshold", the mother/daughter cells association judgment unit 160 judges that this overlapping region is a daughter cell region. For example, the "predetermined threshold" can be set to $\pi \times (w2 \times R)^2$ on the basis of the radius R of the mother cell region. w2 is a predetermined constant which is equal to or more than 0.0 and which is lower than 1.0.

If there are two overlapping regions having areas equal to or more than the predetermined threshold, the mother/daughter cells association judgment unit 160 judges that the cell regions corresponding to the overlapping regions are daughter cell regions resulting from the cell division of the mother cell region (judges that "the mother cell region is associated with the overlapping regions"), and the mother/daughter cells association judgment unit 160 outputs the mother cell ID number, the number of the image in which the mother cell is photographed, the region IDs of the two overlapping regions, and the numbers of the images in which the overlapping regions are photographed, to the association recording unit 170.

At the same time, information which is recorded in the search range recording unit 150 and which is the same as the information output to the association recording unit 170 (the mother cell ID number, the number of the image in which the mother cell is photographed, and the position of the mother cell) is deleted from the search range recording unit 150.

If there are no two overlapping regions having areas equal to or more than the predetermined threshold, the mother/daughter cells association judgment unit 160 stops the processing for the cell image of this frame, and performs judgment processing for the cell images of the following frames.

The association recording unit 170 is a recording medium to which the information (the mother cell ID number of the mother cell region which has been judged that "the mother cell region is associated with the overlapping regions", the number of the image in which the mother cell is photographed, the region IDs of the two overlapping regions, and the numbers of the images in which the overlapping regions are photographed) output from the mother/daughter cells association judgment unit 160 is written.

Figure 10:
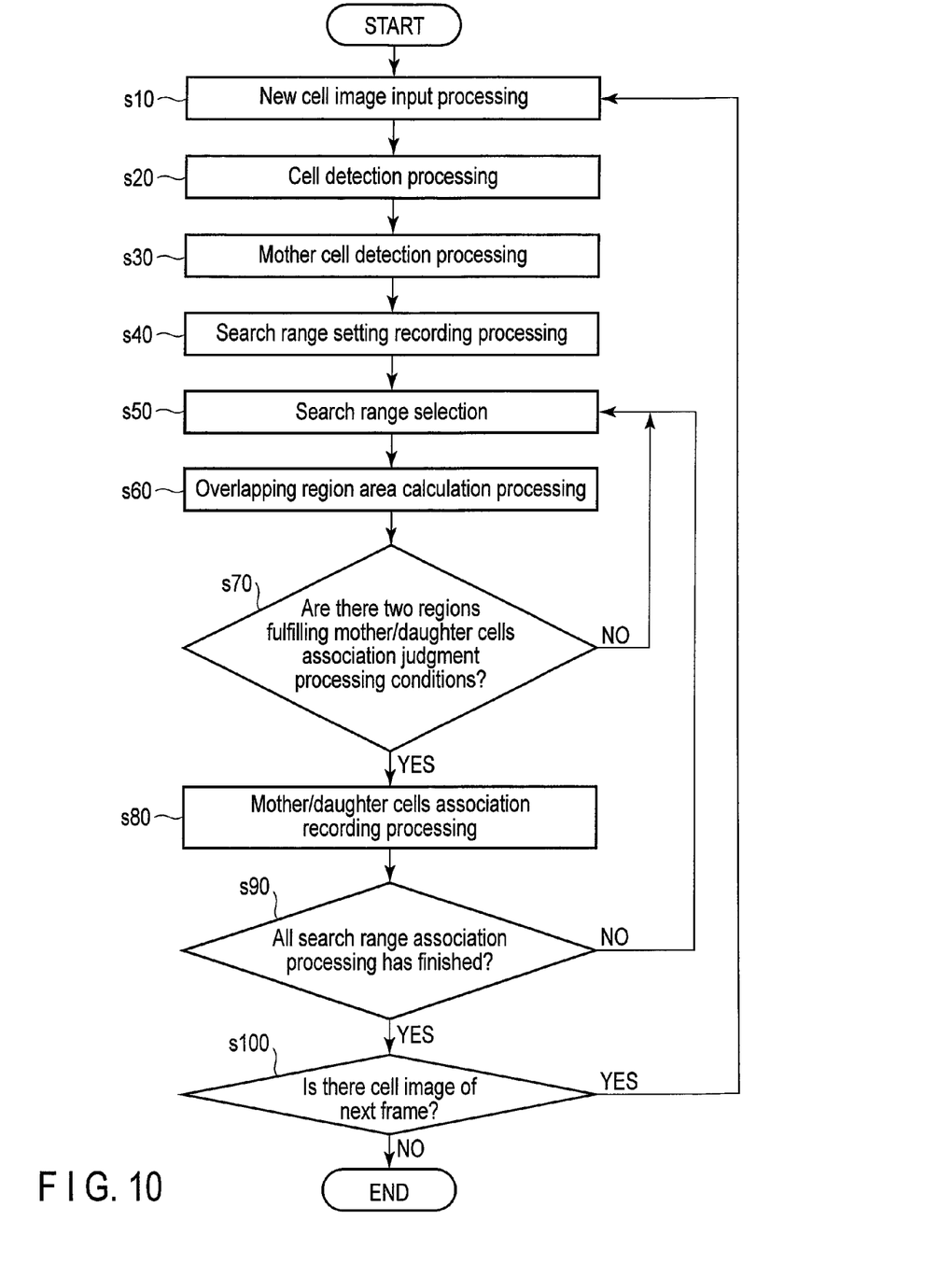
FIG. 10 is a flowchart of cell division tracking processing by the cell division tracking apparatus according to the first embodiment of the present invention.

Now, an example of cell division tracking processing by the apparatus having the above configuration is described. FIG. 10 shows a flowchart of the cell division tracking processing controlled by the control unit 50 of the cell division tracking apparatus according to the first embodiment of the present invention.

The cell detection unit 110 and the mother cell detection unit 120 read a cell image group collected as a result of time-lapse photography by the imaging unit 100 (cell images of an observation target cell group multiple times in a predetermined photography period) (step s10). In this example, the cell detection unit 110 and the mother cell detection unit 120 read a cell image of an image number Ni.

The cell detection unit 110 performs the region dividing processing and the cell detection processing for the read cell image, and classifies generated divided regions into cell regions and background regions to specify individual cell regions (step s20).

The mother cell detection unit 120 performs the mother cell detection processing for the read cell image, detects a mother cell region immediately before cell division, specifies its position and size, and generates positional information and size information (step s30).

The search range initial setting unit 130 sets a search range on the basis of the positional information and size information regarding the mother cell region generated in step S30, and records the set search range in the search range recording unit 150 together with the mother cell ID number of the corresponding mother cell region and the image number of the cell image from which the mother cell region has been detected (step s40).

The control unit 50 selects a search range in which the processing in step S70 has not yet been performed as a processing target search range from among the search ranges set for all the mother cell regions detected by the mother cell detection processing in step S30 (step s50).

The overlapping region area calculation unit 140 detects overlapping regions and calculates their areas (the number of pixels) regarding the search range selected in step S50 (step s60).

The mother/daughter cells association judgment unit 160 judges whether the area of each of the overlapping regions is equal to or more than the predetermined threshold, and judges whether there are two or more overlapping regions having areas equal to or more than the predetermined threshold (step s70).

In other words, the mother/daughter cells association judgment unit 160 judges in step S70 whether the overlapping regions detected in step S60 are daughter cell regions corresponding to daughter cells which have emerged after the division of the mother cell.

If step S70 branches to YES (if the overlapping regions are judged to be daughter cell regions), the association recording unit 170 records the mother cell ID number of the mother cell region, the image number of the cell image in which the mother cell region is photographed, the region IDs of the two overlapping regions, and the image numbers of the cell images in which the overlapping regions are photographed (step s80).

The control unit 50 judges whether the processing in step S70 has been completed for all the mother cell regions detected by the mother cell detection processing in step S30 (step s90). If step S90 branches to NO, that is, if there are mother cell regions for which the processing in step S70 has not yet been performed among the mother cell regions detected in step S30, the control unit 50 proceeds to step S50.

On the other hand, if step S90 branches to YES, that is, if the processing in step S70 has been completed for all the mother cell regions detected by the mother cell detection processing in step S30, the control unit 50 judges whether there is an image number N(i+1) which indicates the cell image of the next frame (step s100).

If step S100 branches to YES, that is, if there is an image number N(i+1) which indicates the cell image of the next frame, the control unit 50 proceeds to step S10. On the other hand, if step S100 branches to NO, the control unit 50 finishes the cell division tracking processing.

Incidentally, if the above-described series of processes of the cell division tracking apparatus according to the present embodiment are programmed or are programmed and then read into a storage medium, this processing is easily sold and distributed as a software product independently of the cell division tracking apparatus, and the technique according to the present embodiment can be used on other hardware.

As described above, according to the present first embodiment, it is possible to provide a cell division tracking apparatus and a cell division tracking program that can accurately track the process of cell division shown in, for example, a cell image group collected by the use of a bright field microscope.

Second Embodiment

Hereinafter, a cell division tracking apparatus and a cell division tracking program according to a second embodiment of the present invention will be described. The differences between the first embodiment and the second embodiment are described to avoid repeated explanations.

Figure 11:
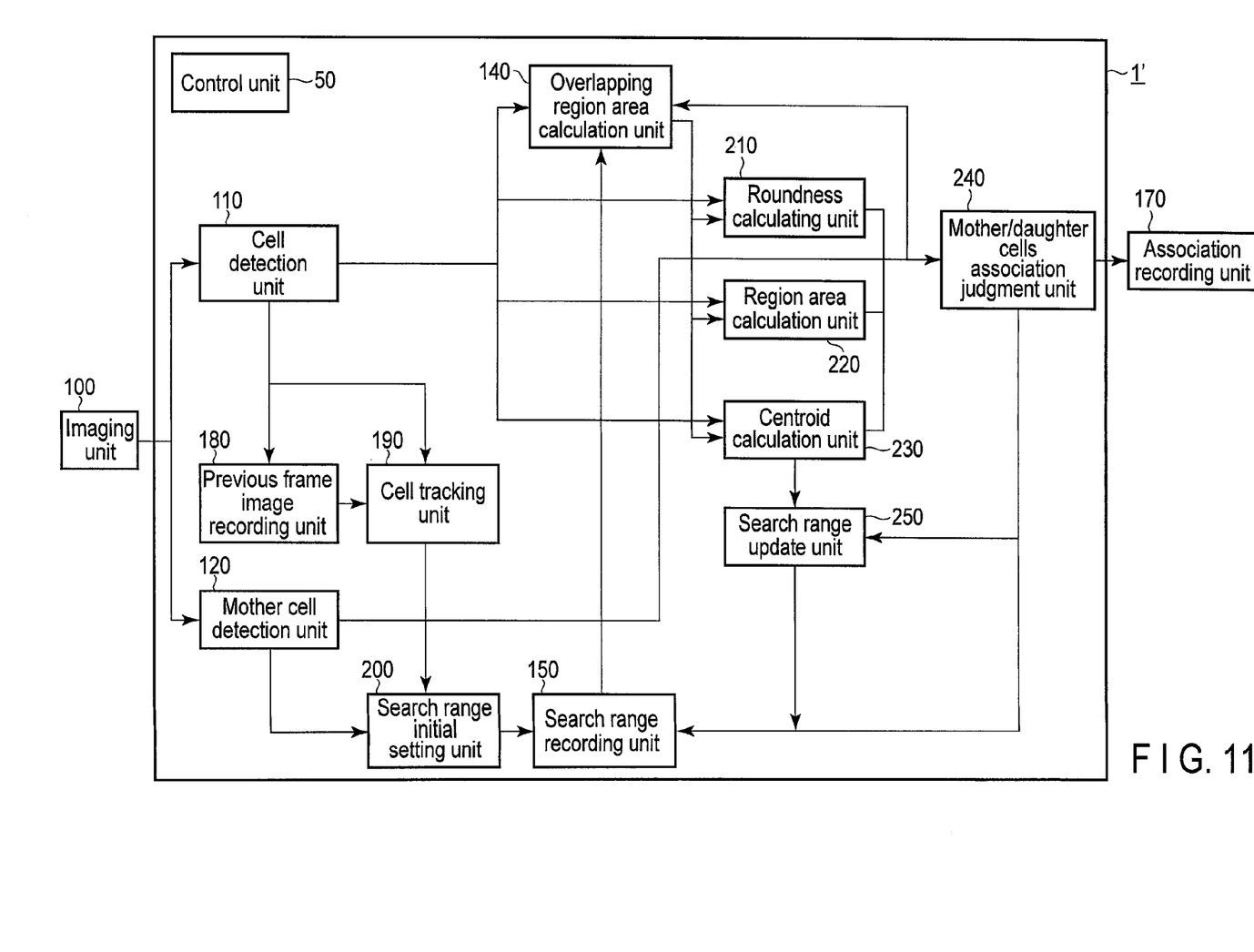
FIG. 11 is a diagram showing a configuration example of a cell division tracking apparatus according to a second embodiment of the present invention.

FIG. 11 is a diagram showing a configuration example of the cell division tracking apparatus. A cell division tracking apparatus (hereinafter referred to as the present apparatus) 1' includes a cell detection unit 110, a mother cell detection unit 120, an overlapping region area calculation unit 140, a search range recording unit 150, a previous frame image recording unit 180, a cell tracking unit (non-division-period cell region detection unit) 190, a search range initial setting unit 200, a roundness calculating unit (feature value calculating unit) 210, a region area calculation unit 220, a centroid calculation unit 230, a mother/daughter cells association judgment unit (non-division-period cell region detection unit) 240, a search range update unit (search range correction unit) 250, and a control unit 50. An imaging unit 100 and an association recording unit 170 are connected to the present apparatus 1'.

The previous frame image recording unit 180 records a region-divided image regarding a cell image (e.g., a cell image of an image number N(i−1)) acquired one frame past a cell image of an image number Ni which is targeted for processing at present. The previous frame image recording unit 180 includes, for example, a recording medium. The previous frame image recording unit 180 updates the contents recorded in the recording medium, that is, the region-divided image at a predetermined timing whenever a new cell image is acquired as a result of imaging by the imaging unit 100. The region-divided image of the cell image of the past frame recorded in the previous frame image recording unit 180 is output to the cell tracking unit 190 before later-described processing by the cell tracking unit 190 is performed.

After the processing by the cell tracking unit 190 is finished, the previous frame image recording unit 180 overwrites and updates the region-divided image regarding the cell image of the image number Ni which has been output from the cell detection unit 110 and which is targeted for processing at present.

The cell tracking unit 190 reads the cell image of the current frame (e.g., the cell image of the image number Ni) from the cell detection unit 110, and also reads the region-divided image of the cell image of the past frame (e.g., the cell image of the image number N(i−1)) from the previous frame image recording unit 180, and compares the region-divided image of the current frame with the region-divided image of the previous frame.

As a result of this comparison, the cell tracking unit 190 specifies a cell region in a "non-cell-division period" which is called an interphase in a cell cycle. The cell tracking unit 190 generates centroid information indicating the centroid of the cell region in the "non-cell-division period", and outputs the centroid information to the search range initial setting unit 200.

In general, the cell in the non-cell-division period irregularly moves between frames and changes its position, but the shape of the cell makes a relatively small change. Using such characteristics, the cell tracking unit 190 performs cell tracking processing in the following manner.

That is, the cell tracking unit 190 calculates the areas (the number of pixels) and centroids of the cell regions in the region-divided image of the current frame and the region-divided image of the past frame. The cell tracking unit 190 detects the cell region whose centroid is closest to the centroid of each cell region in the region-divided image of the current frame among the cell regions in the region-divided image of the past frame, and specifies this region as an "identical cell candidate region".

The cell tracking unit 190 aligns the cell region in the region-divided image of the current frame with the corresponding "identical cell candidate region" so that their centroids correspond to each other, and the cell tracking unit 190 calculates an "overlapping area (the number of pixels)" of these regions.

Here, if the difference between the "overlapping area" and the area of the cell region in the corresponding region-divided image of the current frame is small, the cell tracking unit 190 judges that the "identical cell candidate region" is the cell region of the identical cell.

More specifically, for example, the cell tracking unit 190 judges that the "identical cell candidate region" is the cell region of the identical cell if $$B \times 0.9 < A < B \times 1.0$$

wherein A is the area of the "identical cell candidate region", and B is the area of the cell region in the region-divided image of the current frame.

The "cell region judged to be the cell region of the identical cell" by the cell tracking unit 190 is a cell region in the non-cell-division period which is only moving with a small shape change between the current frame and the past frame. Although described in detail later, the cell region in the non-cell-division period specified as above is excluded from the search range at the time of the setting of the search range.

The search range initial setting unit 200 temporarily sets a search range on the basis of the positional information and size information regarding the mother cell region output from the mother cell detection unit 120.

The search range initial setting unit 200 narrows down (restricts) the search range on the basis of the "centroid of the cell region estimated to be in the non-cell-division period" output from the cell tracking unit 190.

More specifically, the search range initial setting unit 200 excludes the range of a "radius w3×R (w3: a predetermined constant higher than 1.0) from the centroid of the cell region in the non-cell-division period. The search range initial setting unit 200 records the search range thus determined in the search range recording unit 150 together with the mother cell ID number of the corresponding mother cell region and the image number of the cell image from which the mother cell region has been detected.

As described above, in the present second embodiment, if the cell region in the non-cell-division period is included in the search range, this cell region is previously excluded from the search range. Accordingly, the cell tracking unit 190 tracks all the cell regions in the cell image, and the search range initial setting unit 200 excludes the cell region in the non-cell-division period from the search range. In this way, a search range is set so that the regions which can be estimated not to be daughter cell regions are previously excluded. Consequently, the amount of subsequent processing is reduced, and the accuracy of the processing further increases.

The roundness calculating unit 210 calculates a feature value indicating the characteristics of the cell regions. The roundness calculating unit 210 calculates, as the feature value, the "roundness C" of each of the overlapping regions output from the overlapping region area calculation unit 140 on the basis of the region-divided image output from the cell detection unit 110. The roundness calculating unit 210 outputs the roundness C of each of the overlapping regions calculated as the feature value to the mother/daughter cells association judgment unit 240.

This "roundness C" is set so that its value is larger if the shape of the region is closer to a perfect circle.

More specifically, the roundness C can be defined by the following condition (Equation 1):

$$C = 4\pi S/L^2 \qquad \text{(Equation 1)}$$

wherein π indicates the ratio of the circumference of circle to its diameter, S indicates the area of the region, and L indicates the circumferential length of the region.

The region area calculation unit 220 calculates the area of the whole cell region corresponding to each of the overlapping regions output from the overlapping region area calculation unit 140 (i.e., the area of the cell region including (non-overlapping) parts outside the search range on the basis of the region-divided image output from the cell detection unit 110.

The region area calculation unit 220 outputs a region area Sa which is the calculated area (the number of pixels) of the cell region corresponding to each of the overlapping regions to the mother/daughter cells association judgment unit 240.

The centroid calculation unit 230 calculates a centroid Dp which is the centroid of the cell region corresponding to each of the overlapping regions output from the overlapping region area calculation unit 140 on the basis of the region-divided image output from the cell detection unit 110.

The centroid calculation unit 230 outputs the calculated centroid of the cell region corresponding to each of the overlapping regions to the mother/daughter cells association judgment unit 240.

The mother/daughter cells association judgment unit 240 detects a non-division-period cell region corresponding to the cells in the non-cell-division period in the cell images.

The mother/daughter cells association judgment unit 240 updates the search range on the basis of the feature value "roundness C" calculated by the roundness calculating unit 210.

The mother/daughter cells association judgment unit 240 judges whether each overlapping region is a daughter cell resulting from the cell division on the basis of an overlapping area Sr of each overlapping region output by the overlapping region area calculation unit 140, the region area Sa output by the region area calculation unit 220, the centroid Dp output by the centroid calculation unit 230, and the roundness C output by the roundness calculating unit 210.

More specifically, the mother/daughter cells association judgment unit 240 first specifies the two overlapping regions largest in area among the multiple overlapping regions.

The mother/daughter cells association judgment unit 240 then judges whether these two overlapping regions satisfy the following conditions in (Equation 2-1) to (Equation 2-4).

$$Sa > w1 \times \pi R^2 \quad \text{(Equation 2-1)}$$

$$Sr > w2 \times \pi R^2 \quad \text{(Equation 2-2)}$$

$$\|Dp - Mp\| < w3 \times \pi R \quad \text{(Equation 2-3)}$$

$$C < 0.5 \quad \text{(Equation 2-4)}$$

Here, w1, w2, w3 is a predetermined constant, R is size of the mother cell (radius), Mp shows to passion of the mother cell, $\|A-B\|$ shows to distance of between a passion A and a passion B.

If both overlapping regions satisfy the conditions in (Equation 2-1) to (Equation 2-4), the mother/daughter cells association judgment unit 240 judges that the two overlapping regions are daughter cell regions resulting from the division of the mother cell. The mother/daughter cells association judgment unit 240 outputs the mother cell ID number corresponding to these overlapping regions, the image number of the cell image in which the mother cell is photographed, the region IDs of the two overlapping regions, and the image numbers of the cell images in which the overlapping regions are photographed to the association recording unit 170.

Information which is recorded in the search range recording unit 150 and which is the same as the information output to the association recording unit 170 (the mother cell ID number, the number of the image in which the mother cell is photographed, and the position of the mother cell) are deleted from the search range recording unit 150.

If there are no two overlapping regions that satisfy the conditions in (Equation 2-1) to (Equation 2-4), whether at least one of the two overlapping regions targeted for processing satisfies the following conditions in (Equation 3-1) to (Equation 3-4) is judged.

$$Sa > w4 \times \pi R^2 \quad \text{(Equation 3-1)}$$

$$Sr > w5 \times \pi R^2 \quad \text{(Equation 3-2)}$$

$$\|Dp - Mp\| < w6 \times \pi R \quad \text{(Equation 3-3)}$$

$$C < 0.9 \quad \text{(Equation 3-4)}$$

Here, w4, w5, w6 is a predetermined constant, R is size of the mother cell (radius), Mp shows to passion of the mother cell, $\|A-B\|$ shows to distance of between a passion A and a passion B.

If there are no overlapping regions that satisfy (Equation 3-1) to (Equation 3-4), the processing for the cell image of the current frame is stopped, and processing is performed for the cell image of the next frame.

If there is an overlapping region that satisfies the conditions in (Equation 3-1) to (Equation 3-4), this overlapping region can be estimated to be one of the daughter cell regions immediately after the cell division which is smaller in dimension than the mother cell region before cell division and which has a shape close to a perfect circle.

Therefore, the mother/daughter cells association judgment unit 240 changes the search range so that the regions located around the overlapping region that satisfies the conditions in (Equation 3-1) to (Equation 3-4) are easily selected as candidates of daughter cell regions in the processing for the subsequent frames. The mother/daughter cells association judgment unit 240 outputs the centroid of the overlapping region that satisfies the conditions in (Equation 3-1) to (Equation 3-4) to the search range update unit 250.

The search range update unit 250 newly sets, as a search range, a region obtained by excluding the non-division-period cell region from the search range set by the search range initial setting unit (search range setting unit) 130.

On the basis of "the centroid of the overlapping region that satisfies the conditions in (Equation 3-1) to (Equation 3-4)" output from the mother/daughter cells association judgment unit 240, the search range update unit 250 sets, as a new search range, a search range with a concentric region whose central coordinates are at the above centroid and which has a radius R (the radius of the mother cell region). The search range update unit 250 outputs the newly set search range to the search range recording unit 150 to record this search range therein.

Although the cell image photographed by the bright field microscope including the phase contrast microscope is targeted for processing in the present embodiment, the present embodiment may be applied to a cell image photographed by a fluorescence microscope.

Figure 12A:
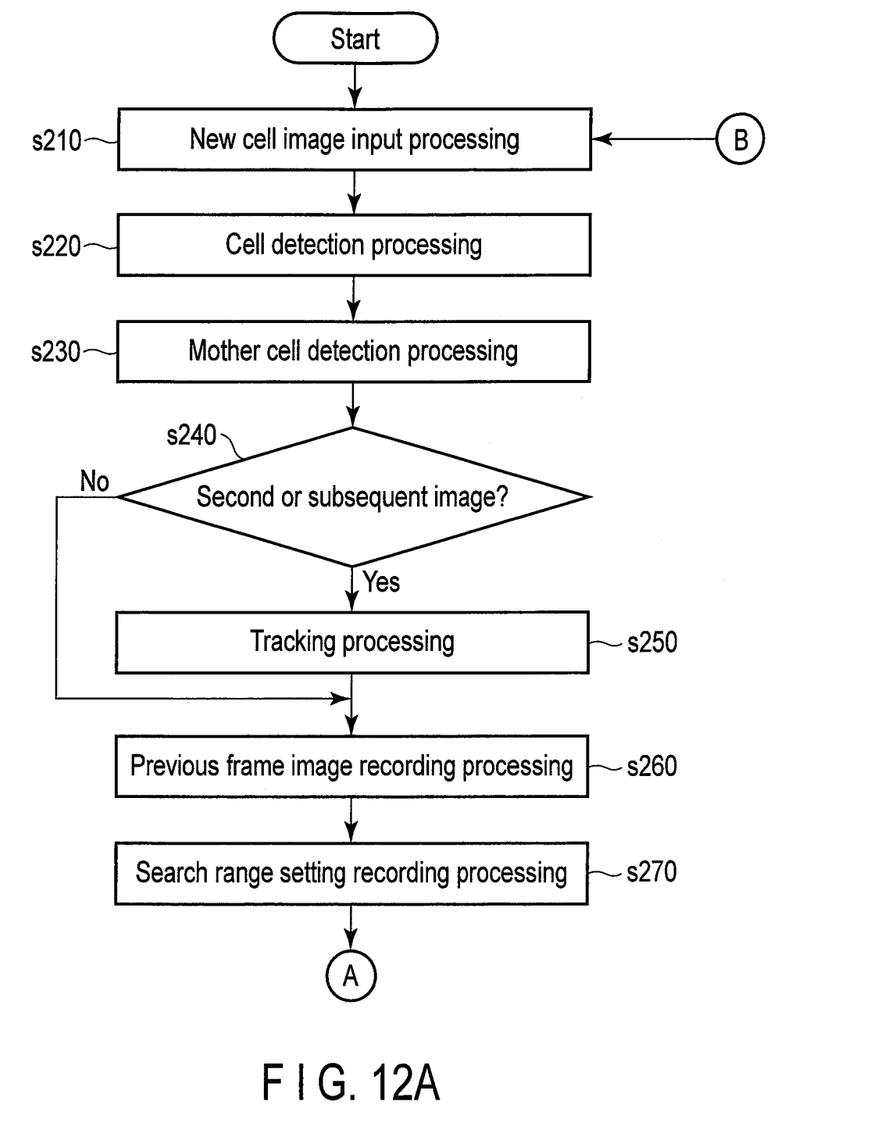
FIG. 12A is a flowchart of cell division tracking processing under the control of a control unit of the cell division tracking apparatus according to the second embodiment of the present invention.
Figure 12B:
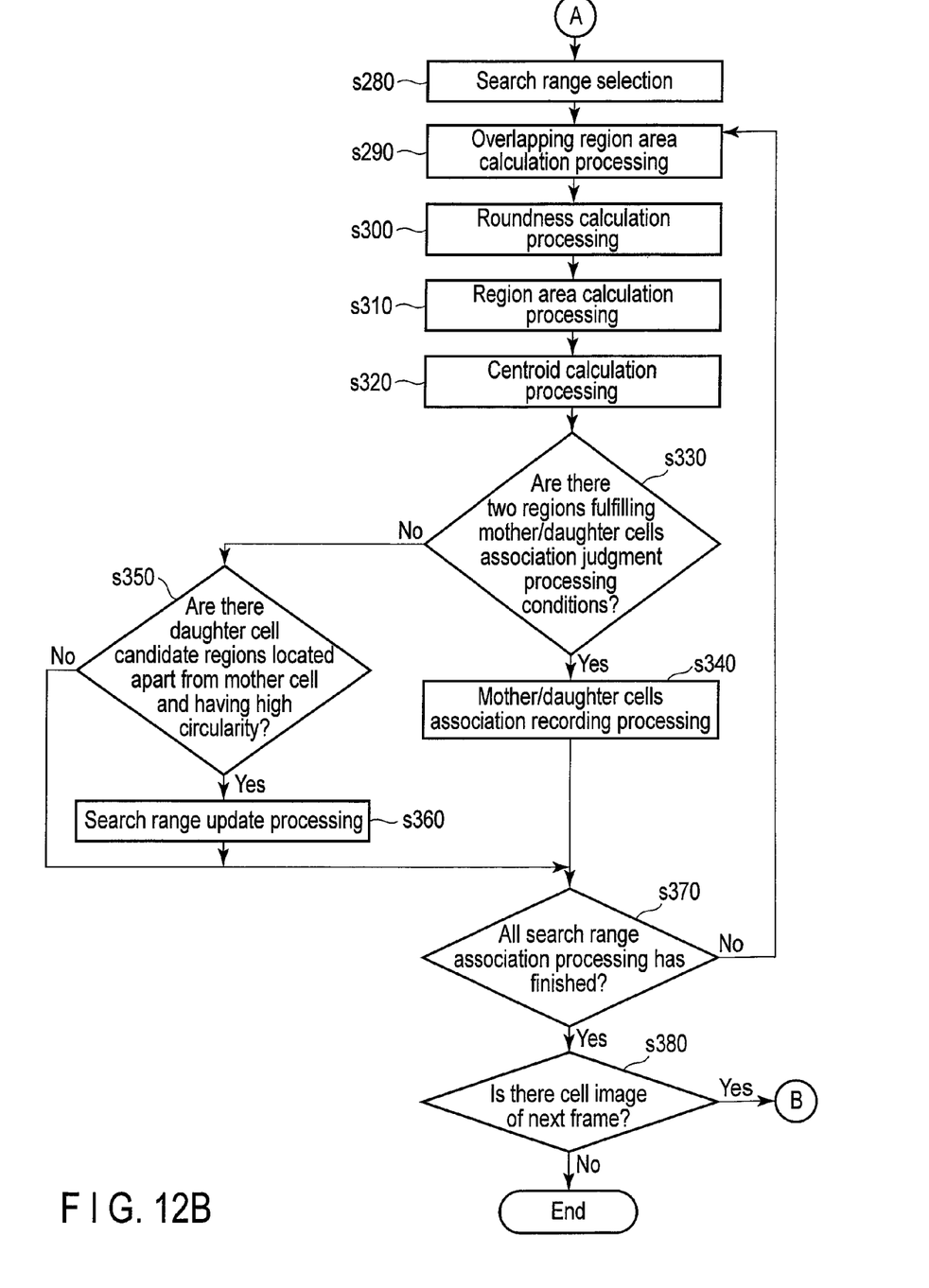
FIG. 12B is a flowchart of the cell division tracking processing under the control of the control unit of the cell division tracking apparatus according to the second embodiment of the present invention.

An example of cell division tracking processing by the cell division tracking apparatus according to the second embodiment of the present invention is described below. FIG. 12A and FIG. 12B show flowcharts of the cell division tracking processing under the control of the control unit 50 of the cell division tracking apparatus according to the second embodiment of the present invention.

The cell detection unit 110 and the mother cell detection unit 120 read a cell image group collected as a result of time-lapse photography by the imaging unit 100 (step s210). In this example, the cell detection unit 110 and the mother cell detection unit 120 read a cell image of an image number Ni.

The cell detection unit 110 performs the region dividing processing and the cell detection processing for the read cell image, and classifies generated divided regions into cell regions and background regions to specify cell regions (step s220).

The mother cell detection unit 120 performs the above-mentioned mother cell detection processing for the read cell image, detects a mother cell region immediately before cell division, specifies its position and size, and generates its positional information and size information (step s230).

The control unit 50 judges whether there is a cell image of an image number N(i−1) which is the previous frame of the processing target image number Ni (whether i≥1) (step s240). If step S240 branches to NO (if i=0), the control unit 50 proceeds to later-described previous frame image recording processing in step S260.

On the other hand, if step S240 branches to YES (if there is a cell image of the image number N(i−1)), the cell tracking unit 190 acquires a region-divided image of the cell image of the current frame (the cell image of the image number Ni) from the cell detection unit 110. The cell tracking unit 190 also acquires a region-divided image of the cell image of the previous frame (the cell image of the image number N(i−1)) from the previous frame image recording unit 180, and compares these region-divided images. As a result of this comparison, the cell tracking unit 190 specifies a cell region in a "non-cell-division period" which is called an interphase in a cell cycle (step s250).

After the processing in step S250 is completed and if step S240 branches to NO, the cell detection unit 110 outputs the region-divided image regarding the cell image of the image number Ni, which is the currant frame, to the previous frame image recording unit 180 as the cell image of the previous frame for the cell image of the next frame, and then records the region-divided image in the previous frame image recording unit 180 (step s260).

If the processing in step S260 is completed, the search range initial setting unit 200 temporarily sets a search range on the basis of the positional information and size information regarding the mother cell region output from the mother cell detection unit 120. The search range initial setting unit 200 then excludes the range of a radius w3×R (w3: a predetermined constant higher than 1.0) from the centroid of the cell region in the non-cell-division period as described above, and sets a search range. The search range initial setting unit 200 records the search range thus set in the search range recording unit 150 together with the mother cell ID number of the corresponding mother cell region and the image number of the cell image from which the mother cell region has been detected (step s270).

The control unit 50 selects a search range in which the mother/daughter cells association judgment processing (later-described processing in step S330) has not yet been performed as a processing target search range from among the search ranges set for all the mother cell regions detected by the mother cell detection processing in step S230 (step s280).

The overlapping region area calculation unit 140 detects overlapping regions and calculates their areas (the number of pixels) regarding the search range selected in step S280 (step s290).

The roundness calculating unit 210 calculates the roundness C of each of the overlapping regions in accordance with (Equation 1) (step s300).

The region area calculation unit 220 calculates a region area Sa which is the area of the whole cell region corresponding to each of the overlapping regions output from the overlapping region area calculation unit 140 on the basis of the region-divided image output from the cell detection unit 110 (step s310).

The centroid calculation unit 230 calculates a centroid Dp of the cell region corresponding to each of the overlapping regions output from the overlapping region area calculation unit 140 on the basis of the region-divided image output from the cell detection unit 110 (step s320).

The mother/daughter cells association judgment unit 240 judges whether the overlapping region is a daughter cell resulting from the division of the mother cell in accordance with (Equation 2-1) to (Equation 2-4) (step s330).

If step S330 branches to YES (if the overlapping region is specified to be a daughter cell region), the association recording unit 170 records the mother cell ID number of the mother cell region, the image number of the cell image in which the mother cell is photographed, the region IDs of the two overlapping regions, and the image numbers of the cell images in which the overlapping regions are photographed (step s340).

On the other hand, if step S330 branches to NO (if the overlapping region cannot be specified to be a daughter cell region), the mother/daughter cells association judgment unit 240 judges whether there is an overlapping region which is smaller in size than the mother cell before cell division and which is estimated to be a daughter cell having a shape close to a perfect circle immediately after the cell division (step s350).

In other words, the mother/daughter cells association judgment unit 240 judges in step S350 whether there is an overlapping region which satisfies (Equation 3-1) to (Equation 3-4) (which is estimated to be a daughter cell).

If step S350 branches to YES (if there is an overlapping region which satisfies (Equation 3-1) to (Equation 3-4) (which is estimated to be a daughter cell), the search range update unit 250 acquires "the centroid of the overlapping region which satisfies (Equation 3-1) to (Equation 3-4)" from the mother/daughter cells association judgment unit 240. Accordingly, the search range update unit 250 sets, as a new search range, a search range with a concentric region whose central coordinates are at the above centroid and which has a radius R (the radius of the mother cell region) (step s360).

Figure 13:
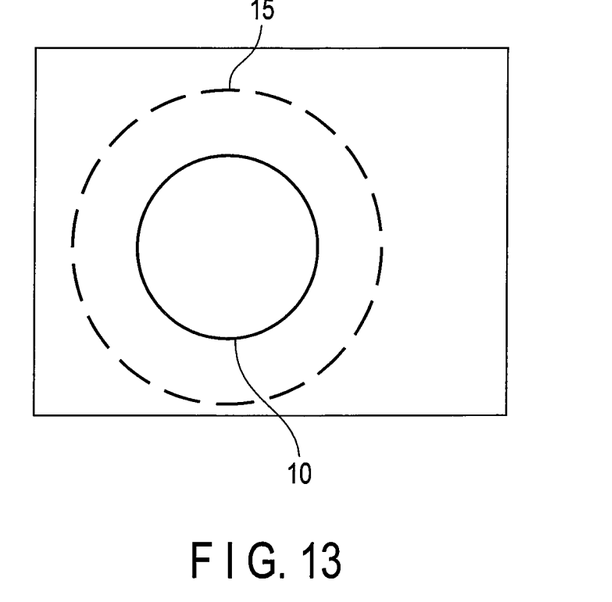
FIG. 13 is a diagram showing a setting example of a search range.
Figure 14:
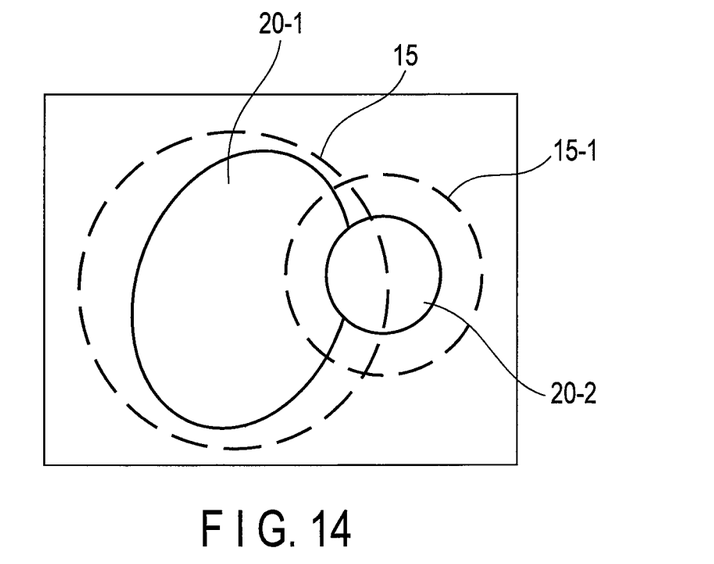
FIG. 14 is a diagram showing a setting example of a search range.

The above-described processing in step S350 and step S360 assumes the following case: For example, if a search range 15 is set for a mother cell region 10 as shown in FIG. 13, two daughter cells (20-1 and 20-2) resulting from the division of the mother cell in the mother cell region 10 are not located at equal distances from the central position of the mother cell in the search range but are located closer to one side as shown in FIG. 14, and one (here 20-2) of the daughter cells is produced at a distance from the position of the mother cell and partly out of the search range 15. In this case, a search range 15-1 is newly set as a search range in addition to the search range 15 so that the cell regions located in the vicinity of the daughter cell 20-2 are easily selected as candidates of daughter cell regions in the processing in step S350 and step S360 for the subsequent frames.

As described above, in the present second embodiment, if there are no two overlapping regions that satisfy the conditions in (Equation 2-1) to (Equation 2-4) (two candidates of daughter cell regions cannot be detected) but there is one cell region that satisfies at least (Equation 3-1) to (Equation 3-4), setting is changed so that the regions around this cell region are newly included in the search range (the setting of the search range is changed until two candidates of daughter cell regions are detected).

After the processing in step S340 or step S360 is completed or if step S350 branches to NO, the control unit 50 judges whether the mother/daughter cells association judgment processing has been conducted for all the mother cell regions detected by the mother cell detection processing in step S230 (step s370).

If step S370 branches to NO (if there are mother cell regions for which the mother/daughter cells association judgment processing has not yet been performed among the mother cell regions detected in step S230, the control unit 50 proceeds to step S280.

On the other hand, if step S370 branches to YES (if the mother/daughter cells association judgment processing in step S230 has been completed for all the mother cell regions detected in step S230), the control unit 50 judges whether there is an image number N(i+1) which indicates the cell image of the next frame (step s380).

If step S380 branches to YES (if there is an image number N(i+1) which indicates the cell image of the next frame), the control unit 50 proceeds to step S210. On the other hand, if step S380 branches to NO, the control unit 50 finishes the cell division tracking processing.

As described above, according to the present second embodiment, it is possible to provide a cell division tracking apparatus and a cell division tracking program which can perform more accurate cell division tracking processing than that performed by the cell division tracking apparatus and the cell division tracking program according to the previously described first embodiment.

While the present invention has been described above in accordance with the first embodiment and the second embodiment, it should be understood that the present invention is not limited to these embodiments and various modifications and applications can be made within the spirit of the invention.

Furthermore, the embodiments described above include various stages of inventions, and various inventions can be extracted by properly combining the disclosed requirements. For example, if some of all the requirements shown in the embodiments are eliminated, a configuration in which those requirements are eliminated can also be extracted as an invention.

What is claimed is:

1. A cell division tracking apparatus comprising:
    an imaging device including an image sensor, which images cells; and
    a system controller which controls the apparatus to:
    image the cells multiple times by the imaging device, and acquire cell images and track division processes of the cells based on a cell image group composed of the cell images;
    detect a cell region in each of the cell images;
    detect a mother cell region corresponding to a mother cell immediately before cell division in each of the cell images;
    set a search range to search for daughter cell regions corresponding to daughter cells resulting from the division of the mother cell based on the mother cell region detected by the mother cell detection unit; and
    judge whether the cell regions are the daughter cell regions based on a region in which the cell regions overlap the search range regarding the cell images collected at and after a detection of the mother cell region.

2. The cell division tracking apparatus according to claim 1, wherein the system controller controls the apparatus to judge that the cell regions are the daughter cell regions if the area of the overlapping region of the cell regions and the search range is equal to or more than a predetermined threshold.

3. The cell division tracking apparatus according to claim 1, wherein the system controller controls the apparatus to judge whether the cell regions are the daughter cell regions based on at least one of a size of an area of an overlapping region of the cell region and the search range, a roundness of the overlapping region, and a centroid of the overlapping region.

4. The cell division tracking apparatus according to claim 1, wherein the system controller controls the apparatus to set the search range based on a position and a size of the mother cell region detected by the mother cell detection unit.

5. The cell division tracking apparatus according to claim 1, the system controller further controls the apparatus to:
    detect a non-division-period cell region corresponding to the cells in a non-cell-division period in the cell images; and
    newly set as a search range, a region obtained by excluding the non-division-period cell region from the search range set by the search range setting unit.

6. The cell division tracking apparatus according to claim 1, the system controller further controls the apparatus to:
    calculate a feature value indicating characteristics of the cell regions; and
    change the search range based on the feature value.

7. The cell division tracking apparatus according to claim 6, wherein the system controller controls the apparatus to calculate a value indicating a roundness of the cell regions as the feature value.

8. The cell division tracking apparatus according to claim 1, wherein the cell image group is obtained by imaging that uses a bright field microscope.

9. A non-transitory computer readable storage medium to store a cell division tracking program, the cell division tracking program enabling:
    an imaging function which images cells;
    a control function which controls the imaging function to images the cells multiple times and acquires a cell images, and tracks division processes of the cells based on a cell image group composed of the cell images;
    a cell detection function which detects a cell region which is a region showing the cells in each of the cell images;
    a mother cell detection function which detects a mother cell region corresponding to a mother cell immediately before cell division in each of the cell images;
    a search range setting function which sets a search range to search for daughter cell regions corresponding to daughter cells resulting from the division of the mother cell based on the mother cell region detected by the mother cell detection function; and
    a daughter cell judgment function which judges whether the cell regions are the daughter cell regions based on a region in which the cell regions overlap the search range regarding the cell images collected at and after a detection of the mother cell region.

* * * * *